(12) United States Patent
Politis et al.

(10) Patent No.: US 11,642,452 B2
(45) Date of Patent: May 9, 2023

(54) PEN NEEDLE CONTAINER

(71) Applicant: Becton, Dickinson and Company, Franklin Lakes, NJ (US)

(72) Inventors: Victor Politis, Natick, MA (US); Mark Bowen, Stow, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 133 days.

(21) Appl. No.: 17/046,194

(22) PCT Filed: Apr. 11, 2019

(86) PCT No.: PCT/US2019/026922
§ 371 (c)(1),
(2) Date: Oct. 8, 2020

(87) PCT Pub. No.: WO2019/204109
PCT Pub. Date: Oct. 24, 2019

(65) Prior Publication Data
US 2021/0069406 A1   Mar. 11, 2021

Related U.S. Application Data

(60) Provisional application No. 62/659,912, filed on Apr. 19, 2018.

(51) Int. Cl.
*A61M 5/00* (2006.01)
*A61M 5/32* (2006.01)

(52) U.S. Cl.
CPC .......... *A61M 5/002* (2013.01); *A61M 5/3202* (2013.01); *A61M 5/3205* (2013.01)

(58) Field of Classification Search
CPC ... A61M 5/002; A61M 5/3202; A61M 5/3205

USPC ....................................................... 206/366
See application file for complete search history.

(56) References Cited

U.S. PATENT DOCUMENTS

| 4,867,309 A | * | 9/1989 | Germain | A61M 5/3205 83/167 |
| 4,875,265 A | * | 10/1989 | Yoshida | A61M 5/3205 29/240 |
| 4,995,871 A | * | 2/1991 | Sasaki | A61M 5/3205 220/348 |
| 5,092,462 A | * | 3/1992 | Sagstetter | A61B 50/362 D34/1 |
| 5,152,394 A | | 10/1992 | Hughes | |
| 5,885,533 A | | 3/1999 | Savage et al. | |
| 6,792,662 B2 | * | 9/2004 | Samuel | A61M 5/3205 29/244 |

(Continued)

FOREIGN PATENT DOCUMENTS

| WO | 2010042680 A1 | 4/2010 |
| WO | 2013068409 A1 | 11/2012 |

*Primary Examiner* — Jacob K Ackun
(74) *Attorney, Agent, or Firm* — Dickinson Wright PLLC

(57) ABSTRACT

A container (10) for storing new and used pen needles (20,30), the container (10) comprising a housing (12) including a first compartment (50) configured to store one or mom new pen needles (20), and a second compartment (52) configured to store one or more used pen needles (30), wherein the first and second compartments (50,52) are inversely adjustable in size to accommodate various combinations of new and used pen needles (20, 30).

17 Claims, 4 Drawing Sheets

(56) References Cited

U.S. PATENT DOCUMENTS

| | | | |
|---|---|---|---|
| 7,337,925 B2* | 3/2008 | Imaizumi | B65D 81/32 |
| | | | 215/6 |
| 8,387,817 B1* | 3/2013 | Zelechonok | B65D 77/065 |
| | | | 137/259 |
| 2003/0132129 A1 | 7/2003 | Erickson | |
| 2005/0113753 A1 | 5/2005 | Alchas et al. | |
| 2005/0269320 A1 | 8/2005 | Erickson et al. | |
| 2005/0269227 A1* | 12/2005 | Erickson | A61M 5/3205 |
| | | | 206/362 |
| 2006/0243635 A1 | 11/2006 | Sullivan et al. | |
| 2008/0128428 A1 | 6/2008 | Beckerman | |
| 2009/0114671 A1 | 5/2009 | Finnestad et al. | |
| 2010/0084406 A1 | 4/2010 | Erickson | |
| 2011/0011881 A1 | 1/2011 | Sansoucy et al. | |
| 2012/0037526 A1 | 2/2012 | Mulone et al. | |
| 2013/0105345 A1 | 5/2013 | Van der Beek et al. | |
| 2014/0210331 A1 | 7/2014 | Tunzi | |
| 2015/0108021 A1 | 4/2015 | Erickson et al. | |
| 2015/0338388 A1 | 11/2015 | Pepe | |
| 2017/0224930 A1 | 8/2017 | Thorne | |

\* cited by examiner

PEN NEEDLE CONTAINER

CROSS-REFERENCE TO RELATED APPLICATION

This application claims priority under 35 U.S.C. 119(e) to U.S. provisional application Ser. No. 62/659,912, filed on Apr. 19, 2018, which is incorporated herein by reference in its entirety.

FIELD OF THE INVENTION

The present invention relates to pen needle containers enclosing new and used pen needles for use with medication delivery pens.

BACKGROUND OF THE INVENTION

It is a well-known practice in the medical community to store pen needles prior to use and subsequently store used pen needles separately from the unused pen needles to avoid contamination. However, size constraints arise and thus an optimized needle storage arrangement is desired.

SUMMARY OF THE INVENTION

It is an aspect of the present invention to provide a pen needle container that reuses the same space to store new and used pen needles while avoiding mixing and contamination. Specifically, a flexible or movable separator separates two compartments that respectively store new and used pen needles. The separator allows the compartments to change in size inversely depending on the number of new and used pen needles being stored.

Another aspect of the present invention provides the compartments made of plastic bags, for example, to provide similar flexibility in size and reduce contamination as described above.

A further aspect of the present invention provides a protective sheath within the container. The protective sheath can engage the flexible separator to protect from fluid contamination into the new pen needle compartment.

Finally, another aspect of the present invention provides a needle bending feature that bends a needle of the used pen needle to disable the needle. The bent needle of the used pen needle also reduces the need for the separator to be puncture resistant.

The foregoing and/or other aspects of the present invention can be achieved by providing a container for storing new and used pen needles, the container comprising a housing including a first compartment configured to store one or more new pen needles, and a second compartment configured to store one or more used pen needles, wherein the first and second compartments are adjustable in size to accommodate various combinations of new and used pen needles.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which.

DETAILED DESCRIPTION OF EXEMPLARY EMBODIMENTS

Figure 1:
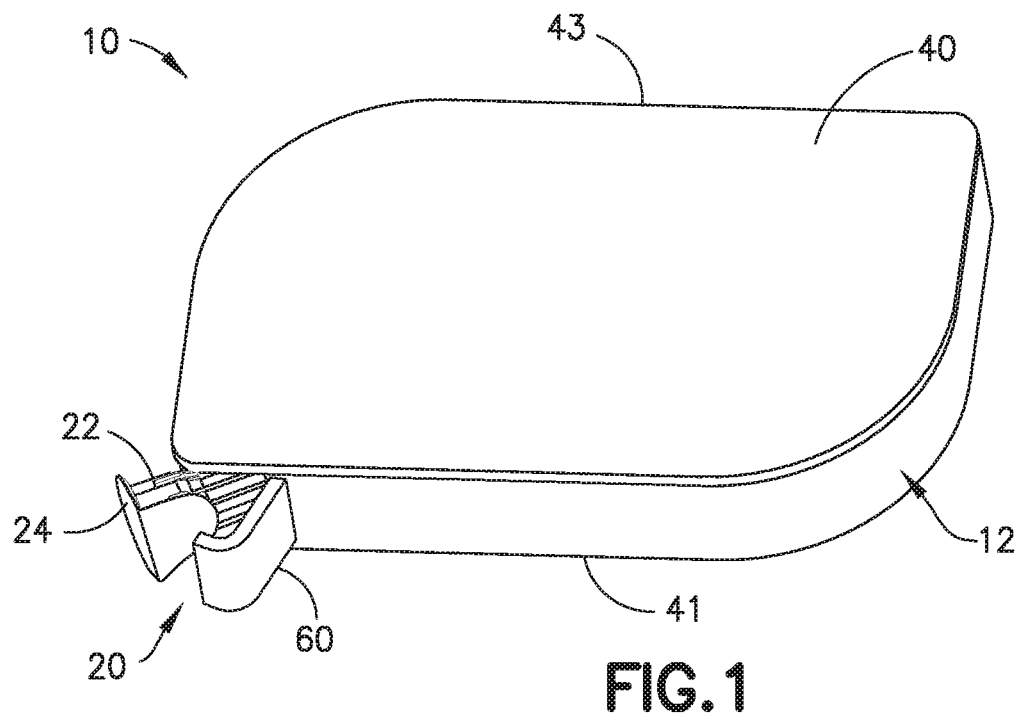
FIG. 1 illustrates a front perspective view of a first exemplary embodiment of a pen needle container.
Figure 2:
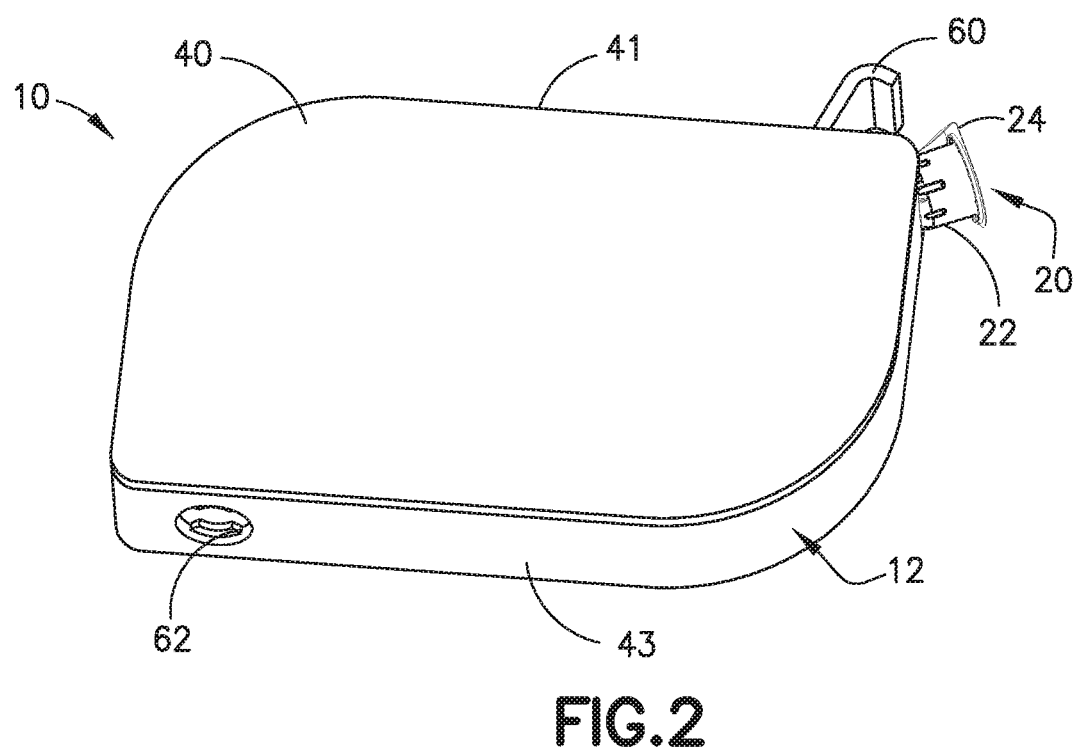
FIG. 2 illustrates a rear perspective view of the pen needle container of FIG. 1.

FIGS. 1 and 2 illustrates the pen needle container 10. The pen needle container 10 includes a housing 12 having a top cover with an outer surface 40, outer side surfaces 41, 43 and an outer bottom surface (not shown). The outer front side surface 41 includes a door 60 to access and remove one or more new pen needles 20 stored in the housing 12.

The outer rear side surface 43 includes an opening 62 to dispose or discard one or more used pen needles 30 into the housing 12. The opening 62 operates similarly to typical sharps containers well-known in the industry. Specifically, the opening 62 engages the hub of a used pen needle 30 while still connected to a medication delivery pen. The user subsequently rotates the medication delivery pen to unscrew the pen needle from the medication delivery pen. Thereafter, the used pen needle 30 enters into the housing 12 and cannot be removed.

The opening 62 is also disposed on an outer surface opposite the door 60. In other words, the outer front side surface 41 and the outer rear side surface 43 are opposite each other. This configuration advantageously prevents confusion between the two access ports by providing adequate separation between the opening 62 and the door 60.

Figure 3:
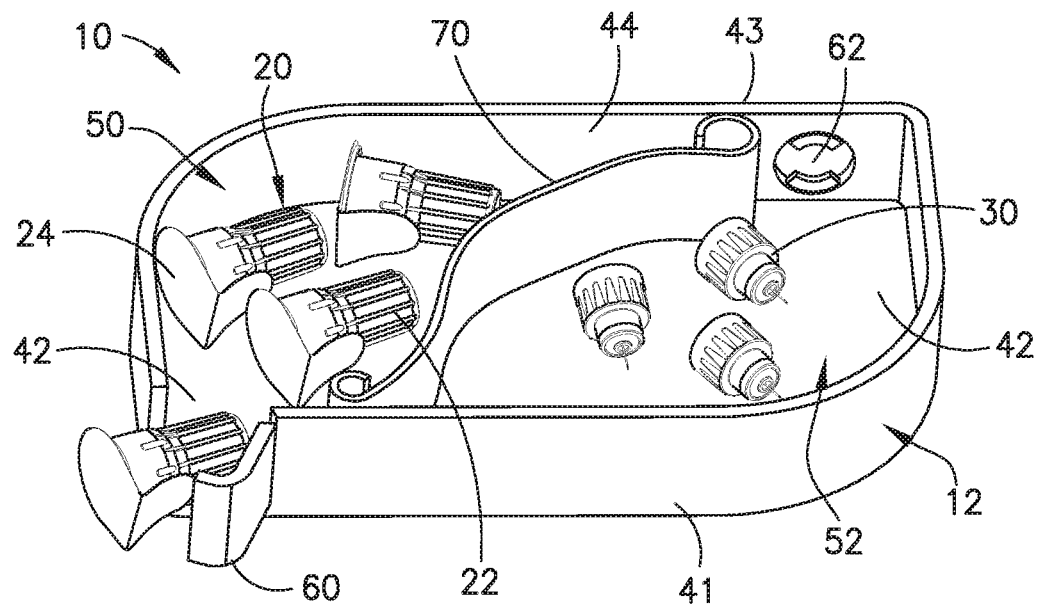
FIG. 3 illustrates a front perspective view of the pen needle container of FIG. 1 with a top cover removed.
Figure 4:
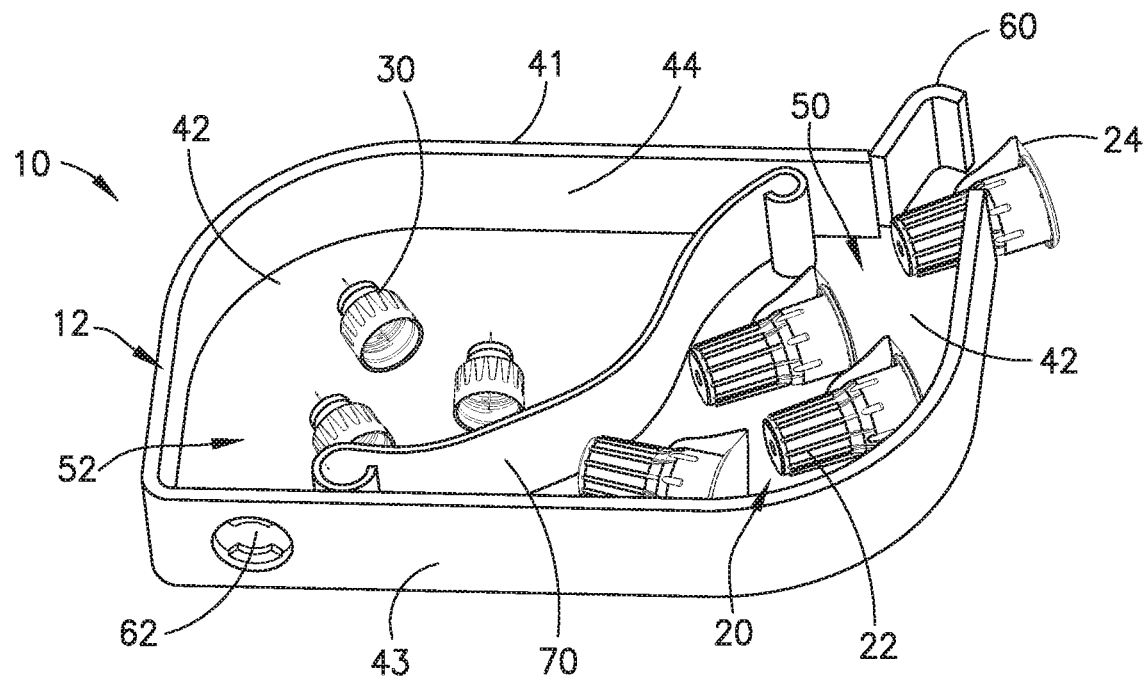
FIG. 4 illustrates a rear perspective view of the pen needle container of FIG. 1 with a top cover removed.
Figure 5:
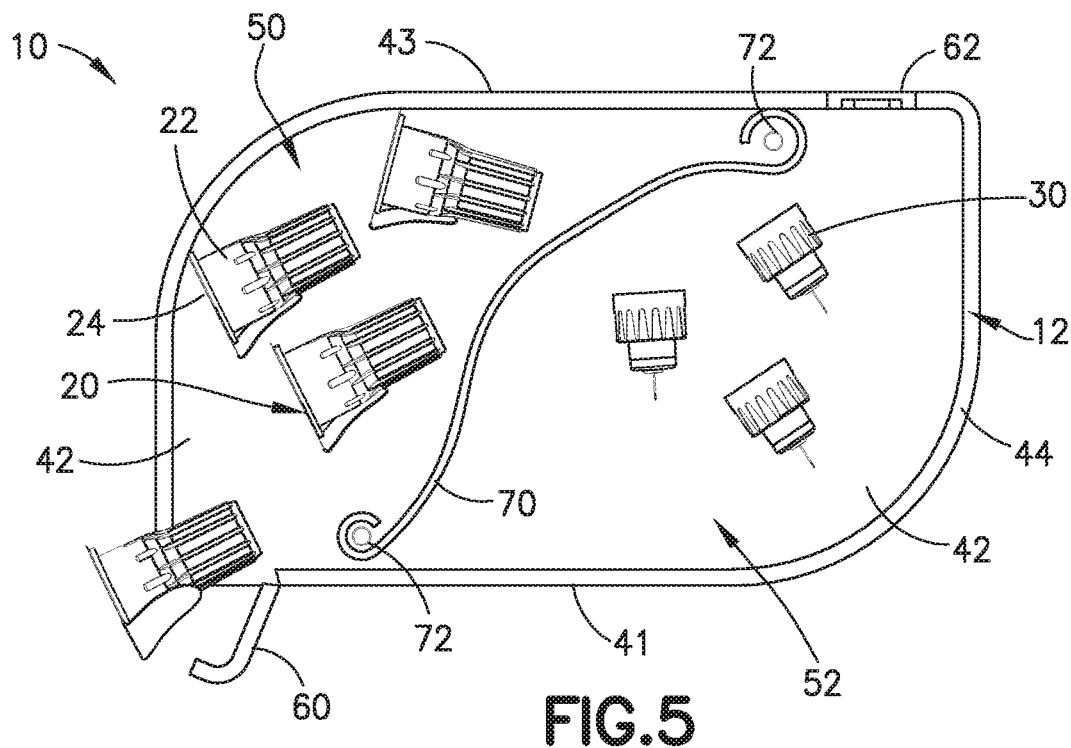
FIG. 5 illustrates a top view of the pen needle container of FIG. 1 with a top cover removed.

FIGS. 3-5 show the pen needle container 10 with the top cover removed to illustrate an inner bottom surface 42 and inner side surfaces 44 of the housing 12. These surfaces 42, 44 support and contain the new and used pen needles 20, 30. These surfaces 42, 44 are enclosed within the housing 12 as illustrated in FIGS. 1 and 2.

FIGS. 3-5 illustrate the new pen needles 20 and the used pen needles 30 within the pen needle container 10. Each of the new pen needles 20 includes a cover 22 and a seal 24 to enclose, seal and package the new pen needle 20. The new pen needles 20 are placed in a first compartment 50 of the pen needle container 10. The first compartment 50 is accessed by the door 60 for the user to remove one of the new pen needles 20.

The cover 22 and the seal 24 are removed for the new pen needle 20 to be attached to the medication delivery pen. Subsequently, the medication delivery pen and the new pen needle 20 are used for medication delivery.

After use, the used pen needle 30 is discarded into a second compartment 52. The second compartment 52 is accessed by the opening 62 for the user to dispose or discard one of the used pen needles 30 as described above.

In one embodiment, the first and second compartments 50, 52 are separated by a flexible separator 70. Such a configuration advantageously provides separate enclosures for the first and second compartments 50, 52. Also, the separator 70 advantageously prevents mixing of the contents, specifically the new and used pen needles 20, 30, in each of the compartments 50, 52. The separator 70 is preferably composed of a flexible elastomeric material and may comprise a strap, a membrane or a fixed rubber band. The separator 70 can also be puncture resistant for additional sealing protection.

The ends of the separator 70 are fixed to the housing 12 via pins 72. Specifically, as illustrated in FIG. 5, the pins 72 are fixed to the inner bottom surface 42 of the housing 12 via a press fit, for example. In a preferred embodiment, the ends of the separator 70 are equipped with looped ends that slip over the pins 72. The ends of the separator 70 are advantageously configured to be free to rotate and not interfere with the movement of the separator 70.

In another embodiment, the separator is engaged to the pins 72 via adhesive, for example. In yet another embodiment, the pins 72 are replaced by cylindrical bars on the ends of the separator 70. The cylindrical bars fit into recesses in the housing 12. The cylindrical bars can be extended to engage holes in the top and bottom surfaces of the housing 12. Although exemplary embodiments are disclosed herein, a variety of securing methods and fixtures are contemplated for the separator 70 in the pen needle container 10.

The separator 70 provides the following advantages. The separator 70 allows the first and second compartments 50, 52 to be flexible or adjustable in size (volume) and not rigid. Such a configuration is advantageous because the number of new and used pen needles 20, 30 will change over the life and use of the pen needles 20, 30 in the pen needle container 10. Accordingly, it is advantageous for the compartments 50, 52 to change in size to accommodate the various combinations of new and used pen needles 20, 30 present in the pen needle container 10.

Another advantage is that when the first and second compartments 50, 52 change in size over the life and use of the pen needles 20, 30 in the pen needle container 10, the first and second compartments 50, 52 are configured to adjust and occupy the same space at different periods of time. In other words, if the first compartment 50 contains seven new pen needles 20 and the second compartment 52 contains no used pen needles 30, the separator 70 flexes and makes the first compartment 50 larger and the second compartment 52 smaller. Based on the configuration illustrated in FIGS. 3-5, the first compartment 50 would be larger than the second compartment 52.

On the other hand, if the second compartment 52 contains seven used pen needles 30 and the first compartment 50 contains no new pen needles 20, the separator 70 flexes and makes the second compartment 52 larger and the first compartment 50 smaller. Based on the configuration illustrated in FIGS. 3-5, the second compartment 52 would be larger than the first compartment 50.

The movement of the separator 70 due to its flexibility allows for the use or overlap of the same space at different times when the first compartment 50 expands and when the second compartment 52 expands. This is because while one compartment expands, the other compartment shrinks in inverse relationship, and vice-versa, with the total volume of the container 10 remaining the same. This occurs throughout the life and use of the pen needle container 10. That is, the first and second compartments 50, 52 are capable of sharing the same space at different times. Such a configuration provides compactness of the pen needle container 10, reduces the overall size when compared to having two rigid (fixed size) compartments, and optimizes the available space in the pen needle container 10 while reducing the amount of empty space (unused space) at any given time.

Any size and shape of the pen needle container 10 and any combination of new and used pen needles 20, 30 is contemplated by this disclosure while providing similar advantages described herein. For example, according to one embodiment, the pen needle container 10 includes a plurality of new pen needles 20 and no used pen needles 30. According to another embodiment, the pen needle container 10 includes a plurality of used pen needles 30 and no new pen needles 20. In another embodiment, the pen needle container 10 includes a plurality of used pen needles 30 and a plurality of new pen needles 20.

Figure 6:
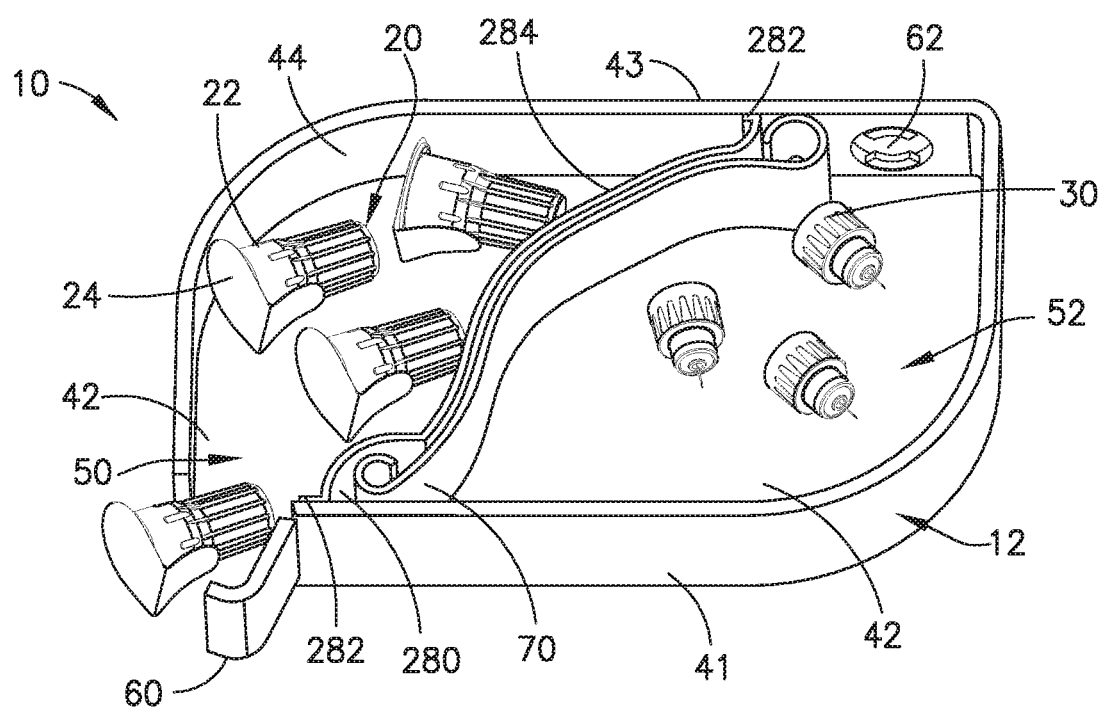
FIG. 6 illustrates a front perspective view of a second exemplary embodiment of the pen needle container having a sheath and with a top cover removed.

FIG. 6 illustrates a second embodiment of the pen needle container 10. This embodiment includes all the features of FIGS. 1-5 with the addition of a protective sheath 280. In a preferred embodiment, the protective sheath 280 and the separator 70 are both fixed to the housing 12 and not to each other. This configuration advantageously allows the protective sheath 280 and the separator 70 to move relative to each other.

The protective sheath 280 is also fixed to an inner surface of the housing 12. Specifically, the protective sheath 280 includes two end flanges 282, a top surface 284 and a bottom surface (not visible). The end flanges 282 are fixed and sealed to the inner side surfaces 44 of the housing 12 by one of an adhesive, welding, heat staking, rivets and a snap-fit assembly, for example.

The top surface 284 of the protective sheath 280 is sealed to an inner top surface (not shown), opposing the outer top surface 40 of the housing 12. The bottom surface (not shown) of the protective sheath 280 is also sealed to the inner bottom surface 42 of the housing 12. In this manner, the protective sheath 280 is sealed to the top and bottom inner surfaces 42 of the housing 12 via compression, similar to the function of an O-ring compressed and sealed between two surfaces.

The protective sheath 280 is disposed within the first compartment 50 to advantageously reduce contamination and protects biohazards from mixing with the new pen needles 20 in the first compartment 50. The protective sheath 280 also provides fluid absorption protection and minimizes contamination entering from the second compartment 52 to the first compartment 50.

In an alternate embodiment, the protective sheath 280 is fixed to the separator 70 via heat staking or adhesive, for example, and cooperates with the separator 70 by moving and flexing together. Accordingly, the protective sheath 280 and the separator 70 act as a unitary part.

In another embodiment, at least one of the first and second compartments 50, 52 includes a plastic bag sealed to the inner surface of the housing 12. In this configuration, a protective sheath 280 is not needed. This is due to the self-sealing nature of one of the compartments 50, 52 since the contents of the one compartment is enclosed by the plastic bag. That is, no contamination can pass between the two compartments 50, 52 when one of the compartments is a plastic bag.

Figure 7:
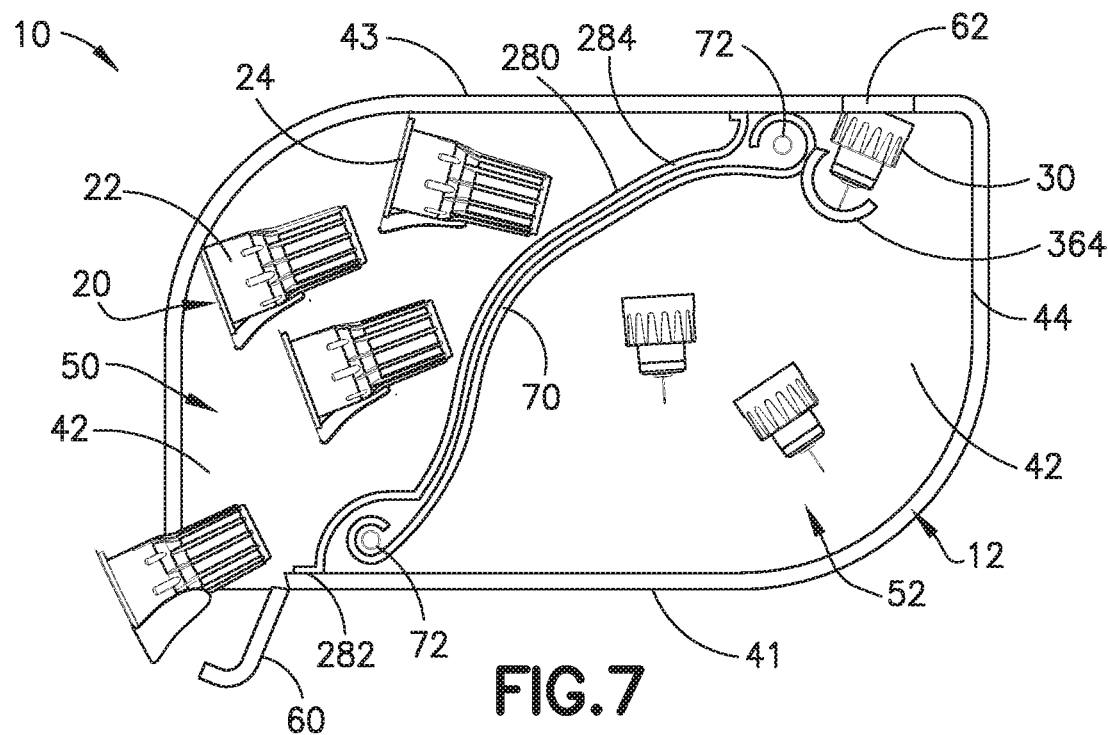
FIG. 7 illustrates a top view of a third exemplary embodiment of the pen needle container having a needle bending feature and with a top cover removed.
Figure 8:
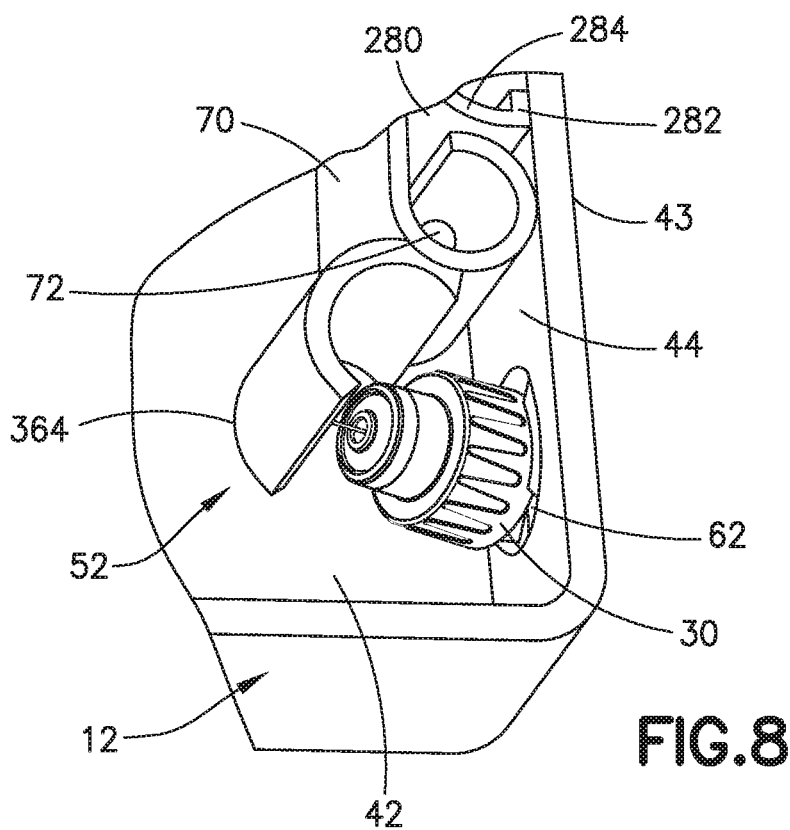
FIG. 8 illustrates a partial perspective view of the needle bending feature of FIG. 7.

FIGS. 7 and 8 illustrate a third embodiment of the pen needle container 10 incorporating one or both of the first and second embodiments described above and further including a needle bending feature 364. The needle bending feature 364 is configured to bend and disable a needle of the one or more used pen needles 30 while it enters the opening 62 for disposal.

Specifically, the needle bending feature 364 includes a curved or angled surface that is fixed to an interior of the housing 12 and is adjacent to the opening 62. In another embodiment, the needle bending feature 364 is integral to the housing 12. The curved surface of the needle bending feature 364 advantageously engages the needle of the used pen needle 30 at a variety of angles to successfully bend the needle.

Preferably, the opening 62 is configured to include a cylindrical guidance path. The cylindrical guidance path extends into the second compartment 52 to advantageously ensure that the needle of the used pen needle 30 is directed toward the needle bending feature 364.

In operation, when a used pen needle 30 is disposed in the second compartment 52 of the housing 12, the used pen needle 30 first enters into the opening 62. Immediately, the needle of the used pen needle 30 contacts the needle bending feature 364. The needle bending feature 364 is specifically positioned in the housing 12 to force engagement to the needle of the used pen needle 30. The user pushes and applies pressure to the used pen needle 30 into the opening 62 and into the needle bending feature 364.

As a result of the pressured applied by the user, the needle bending feature 364 bends the needle of the used pen needle 30. That is, the needle is bent back toward the hub of the used pen needle 30. In other words, the opening 62 and the needle bending feature 364 in the housing 12 are configured so that the needle of the used pen needle 30 is guided and forced against the needle bending feature 364 to cause the needle to bend. Accordingly, the needle of the used pen needle 30 is sufficiently bent and disabled from further use.

After being disabled, the used pen needle 30 is reduced in length via the bent needle to provide additional clearance. Thus, the used pen needle 30 is able to disengage the needle bending feature 364 via the clearance and fully enter into the second compartment 52 for disposal. In other words, once a hub of the used pen needle 30 is pushed far enough through the opening 62 and into the housing 12 to ensure complete needle bending, the used pen needle 30 is free to enter the second compartment 52.

Disabling of the used pen needle 30 advantageously reduces puncturing of the separator 70 and/or the protective sheath 280, as might otherwise occur when many used pen needles 30 are present in the second compartment 52 in a closely packed configuration. Further, the need for the separator 70 and/or the protective sheath 280 to be puncture resistant is reduced.

In another embodiment similar to the embodiments disclosed above but not illustrated, the separator 70 is rigid and movable. Specifically, the separator 70 is fixed to pins 72 similar to those of FIGS. 5-7, but in this case the pins 72 are movably engaged with and travel in grooves disposed along the inner top surface (not shown) and the inner bottom surface 42 of the housing 12. Accordingly, when the first compartment 50 expands and the second compartment 52 shrinks, the separator 70 moves or slides to the right via the pins 72 and the grooves. On the other hand, when the second compartment 52 expands and the first compartment 50 shrinks, the separator 70 moves or slides to the left via the pins 72 and the grooves. The engagement between the pins 72 and the grooves is very precise to reduce contamination from passing through, as well as to provide smooth movement of the separator 70 without jamming.

In another non-illustrated embodiment, the separator 70 pivots or rotates instead of slides to enlarge and shrink the first and second compartments 50, 52 accordingly. For example, one of the pins 72 is rotatably fixed to the separator 70 and the housing 12, while the other pin 72 moves along a curvilinear groove in the housing 12. In operation, one of the pins 72 moves along a curvilinear groove in the housing 12 to move the separator 70 and thereby enlarge and shrink the first and second compartments 50, 52, accordingly. The other pin 72 is fixed but rotates in place to reduce the strain during the movement of the separator 70.

In yet another non-illustrated embodiment, the separator 70 is made of several segments that telescope over each other. While each segment may be rigid, the separator 70 can flex in shape and change its length during movement to advantageously provide a more effective physical separation of the first and second compartments 50, 52.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

What is claimed is:

1. A container for storing new and used pen needles, the container comprising:
   a housing including:
      a first compartment configured to store one or more new pen needles;
      a second compartment configured to store one or more used pen needles;
      a flexible separator that separates the first compartment from the second compartment; and
      a protective sheath fixed to the housing and within the first compartment to reduce contamination, the protective sheath including end flanges that are fixed to inner side surfaces of the housing; wherein
   the first and second compartments are adjustable in size to accommodate various combinations of new and used pen needles.

2. The container according to claim 1, wherein the first and second compartments are configured to change in size inversely while maintaining the total size of the container at the same time.

3. The container according to claim 1, wherein the flexible separator moves to accommodate the various combinations of new and used pen needles.

4. The container according to claim 1, wherein the protective sheath includes a top surface and a bottom surface that are compressed and sealed to a top and bottom inner surface of the housing.

5. The container according to claim 1, wherein the first and second compartments are capable of occupying a same space.

6. The container according to claim 1, wherein the first and second compartments are separately enclosed without mixing the new and used pen needles.

7. The container according to claim 1, wherein the various combinations includes a plurality of new pen needles and no used pen needles.

8. The container according to claim 1, wherein the various combinations includes a plurality of used pen needles and no new pen needles.

9. The container according to claim 1, further comprising a door to access and remove the one or more new pen needles from the housing.

10. The container according to claim 9, further comprising
an opening to dispose the one or more used pen needles into the housing; wherein
the opening is disposed on an outer surface of the housing opposite the door.

11. The container according to claim 1, further comprising a needle bending feature that is configured to bend a needle of the one or more used pen needle.

12. The container according to claim 11, wherein the needle bending feature includes a curved surface fixed adjacent to an opening.

13. The container according to claim 11, wherein when the one or more used pen needles is disposed into an opening and engages the needle bending feature, the needle of the used pen needle is bent before disengaging the needle bending feature and fully entering the second compartment.

14. The container according to claim 11, wherein the needle bending feature is integral to the housing.

15. The container according to claim 11, wherein the needle bending feature is configured such that the needle is undivided from the used pen needle after the needle is bent.

16. A container for storing new and used pen needles, the container comprising:
a housing including:
a first compartment configured to store one or more new pen needles;
a second compartment configured to store one or more used pen needles;
a flexible separator that separates the first compartment from the second compartment; and
one or more pins that fix ends of the flexible separator to the housing; wherein
the first and second compartments are adjustable in size to accommodate various combinations of new and used pen needles.

17. The container according to claim 16, further comprising
two or more pins that fix the separator to the housing, wherein
the two or more pins move along grooves of the housing to adjust the size of the first and second compartments.

\* \* \* \* \*